United States Patent [19]

Matsutani et al.

[11] Patent Number: 5,022,857
[45] Date of Patent: Jun. 11, 1991

[54] DENTAL BURR AND DENTAL HANDPIECE

[75] Inventors: Kanji Matsutani, Takanezawa; Masatoshi Fukuda, Utsunomiya, both of Japan

[73] Assignee: Matsutani Seisakusho Co., Ltd., Tochigi, Japan

[21] Appl. No.: 287,116

[22] Filed: Dec. 21, 1988

[51] Int. Cl.⁵ .............................................. A61C 1/12
[52] U.S. Cl. ..................................... 433/85; 433/127
[58] Field of Search ............... 433/84, 85, 115, 126, 433/127, 132, 165, 166, 132

[56] References Cited

U.S. PATENT DOCUMENTS

| | | | |
|---|---|---|---|
| 2,442,033 | 5/1948 | Brantley et al. | 433/82 |
| 3,136,059 | 6/1964 | Nelson | 433/127 |
| 3,175,293 | 3/1965 | Borden | 433/127 |
| 3,393,452 | 7/1968 | Nelson | 433/166 |
| 3,624,905 | 12/1971 | Barsby | 433/82 |
| 3,762,052 | 10/1973 | Melde | 433/120 |
| 3,778,904 | 12/1973 | Melde | 433/120 |
| 3,842,632 | 10/1974 | Nelson | 433/165 |
| 3,871,097 | 3/1975 | Melde | 433/82 |
| 3,969,822 | 7/1976 | Fukuyama | 433/132 |
| 4,021,919 | 5/1977 | Lingenhole et al. | 433/132 |
| 4,021,920 | 5/1977 | Kirschner | 433/82 |
| 4,153,993 | 5/1979 | Kataoka | 433/132 |
| 4,484,892 | 11/1984 | Pernot et al. | 433/132 |
| 4,493,645 | 1/1985 | Nakanishi | 433/127 |
| 4,533,324 | 8/1985 | Nakanishi | 433/132 |
| 4,536,157 | 8/1985 | Maizenberg | 433/129 |
| 4,575,338 | 3/1986 | Maizenberg | 433/126 |
| 4,869,668 | 9/1989 | Seney | 433/85 |
| 4,874,314 | 10/1989 | Fleer et al. | 433/127 |

FOREIGN PATENT DOCUMENTS

| | | | |
|---|---|---|---|
| 944517 | 6/1956 | Fed. Rep. of Germany. | |
| 1541216 | 3/1970 | Fed. Rep. of Germany. | |
| 2331023 | 1/1975 | Fed. Rep. of Germany. | |
| 3433570 | 3/1986 | Fed. Rep. of Germany | 433/165 |
| 2473303 | 7/1982 | France | 433/115 |
| 2509985 | 1/1983 | France. | |
| 56-51845 | 12/1981 | Japan. | |
| 58-65152 | 4/1983 | Japan. | |
| 383546 | 1/1965 | Switzerland | 433/132 |
| 920096 | 3/1963 | United Kingdom | 433/115 |

Primary Examiner—John J. Wilson
Assistant Examiner—Frank A. LaViola
Attorney, Agent, or Firm—Fish & Richardson

[57] ABSTRACT

A dental burr has an axis of rotation and a cooling water passage extending therethrough in coaxial relation to the dental burr. The cooling water passage opens to a front end face of the dental burr, and this opening in the front end of the dental burr is disposed in an area including the axis of rotation of the dental burr. A dental handpiece for rotatably holding a dental burr includes a handgrip portion, a hollow head portion provided at a front end of the handgrip portion, and a cooling water passage. This cooling water passage extends along the handgrip portion, and opens at one end to a rear end of the handgrip portion while the other end thereof is connected to an internal space of the head portion. Part of the internal space serves as a passage for communicating the cooling water passage of the dental handpiece with the cooling water passage of the dental burr held by the dental handpiece.

10 Claims, 9 Drawing Sheets

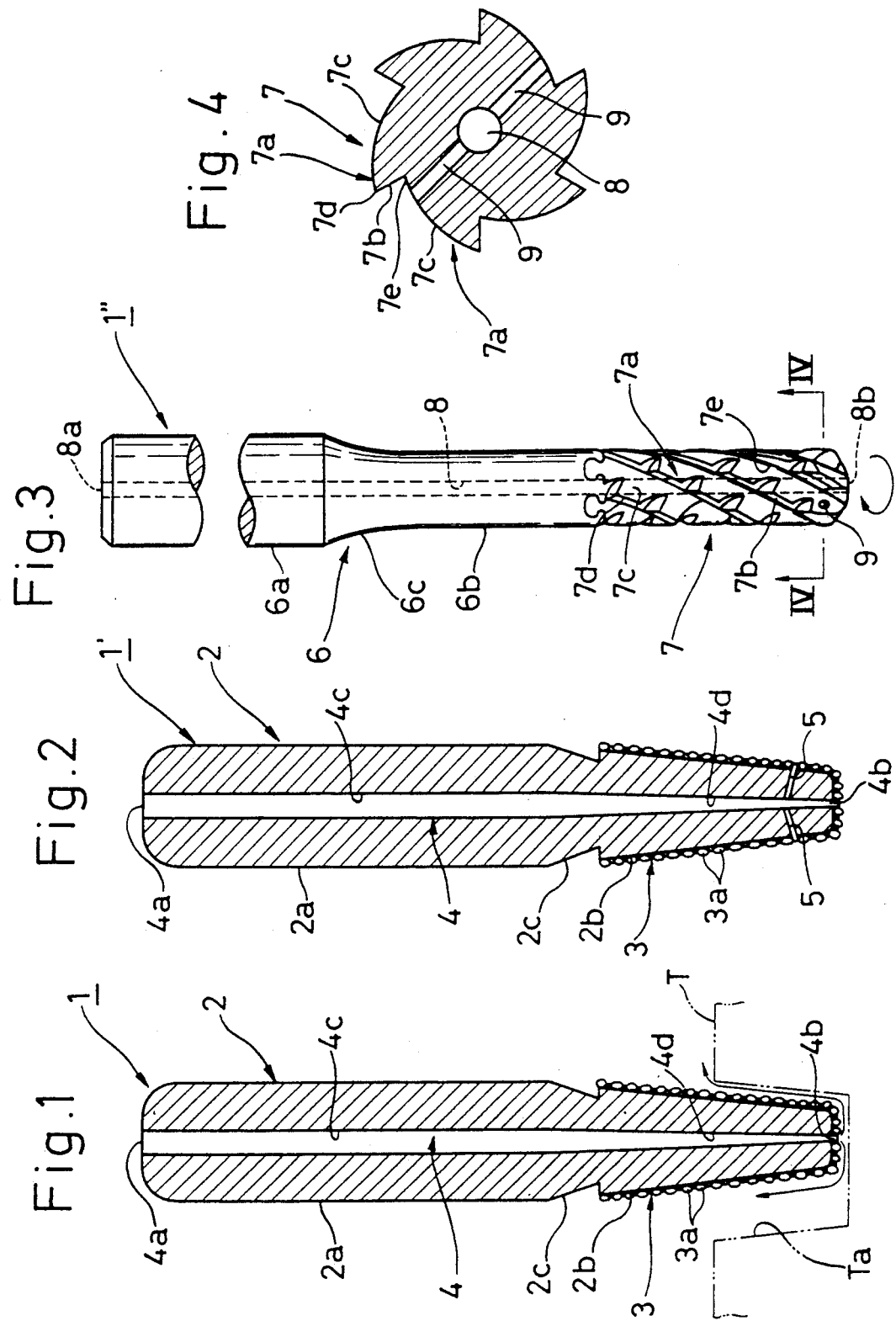

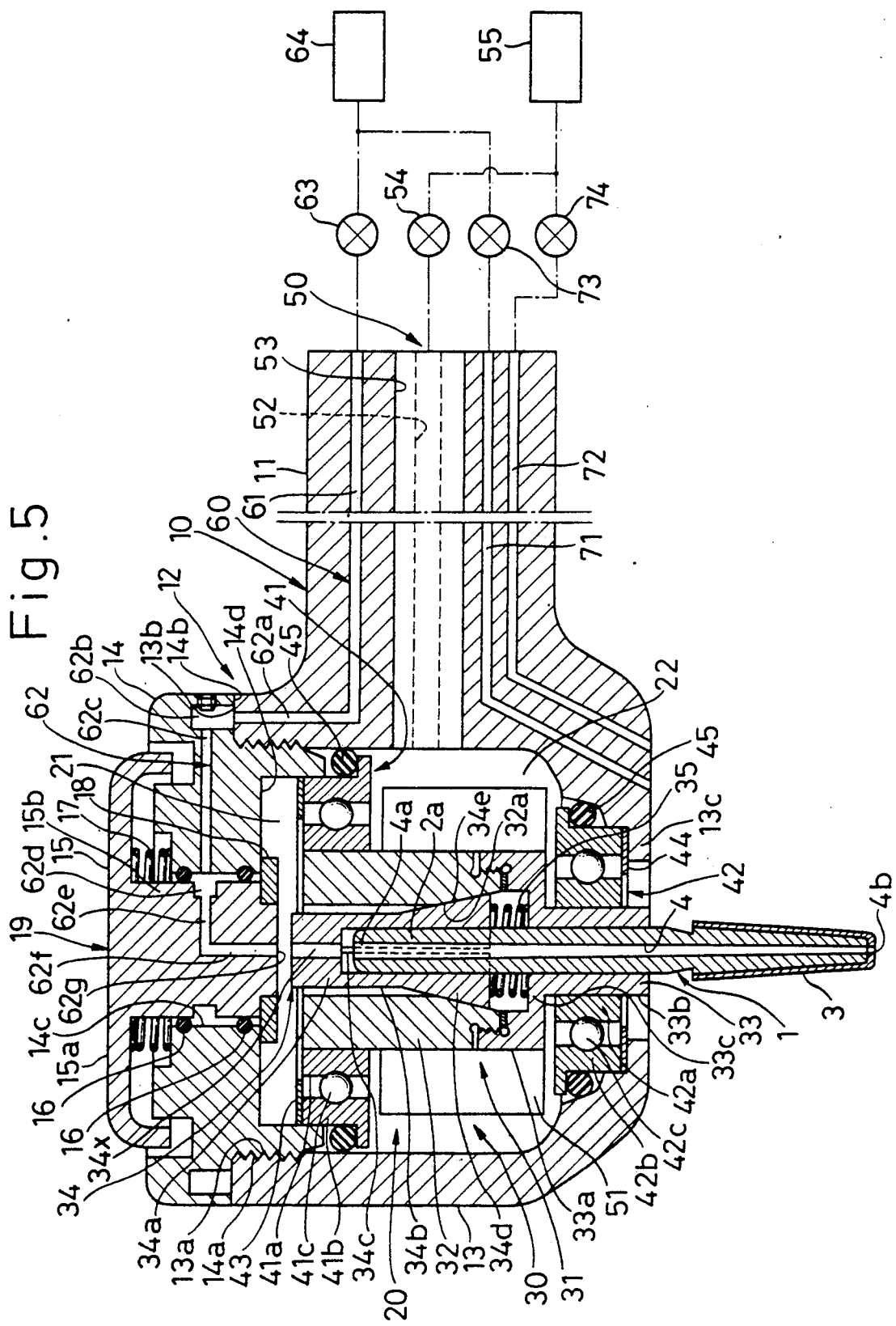

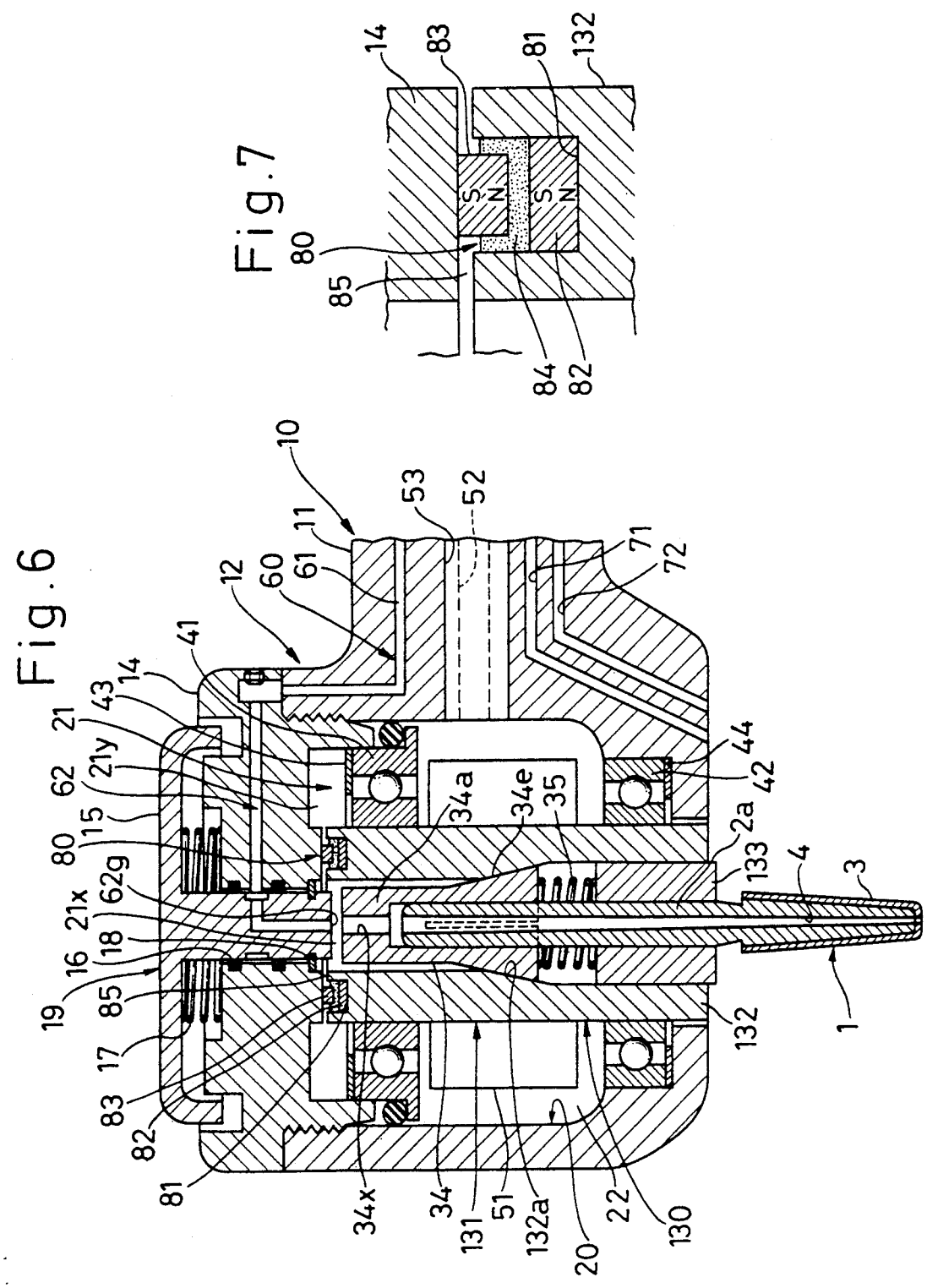

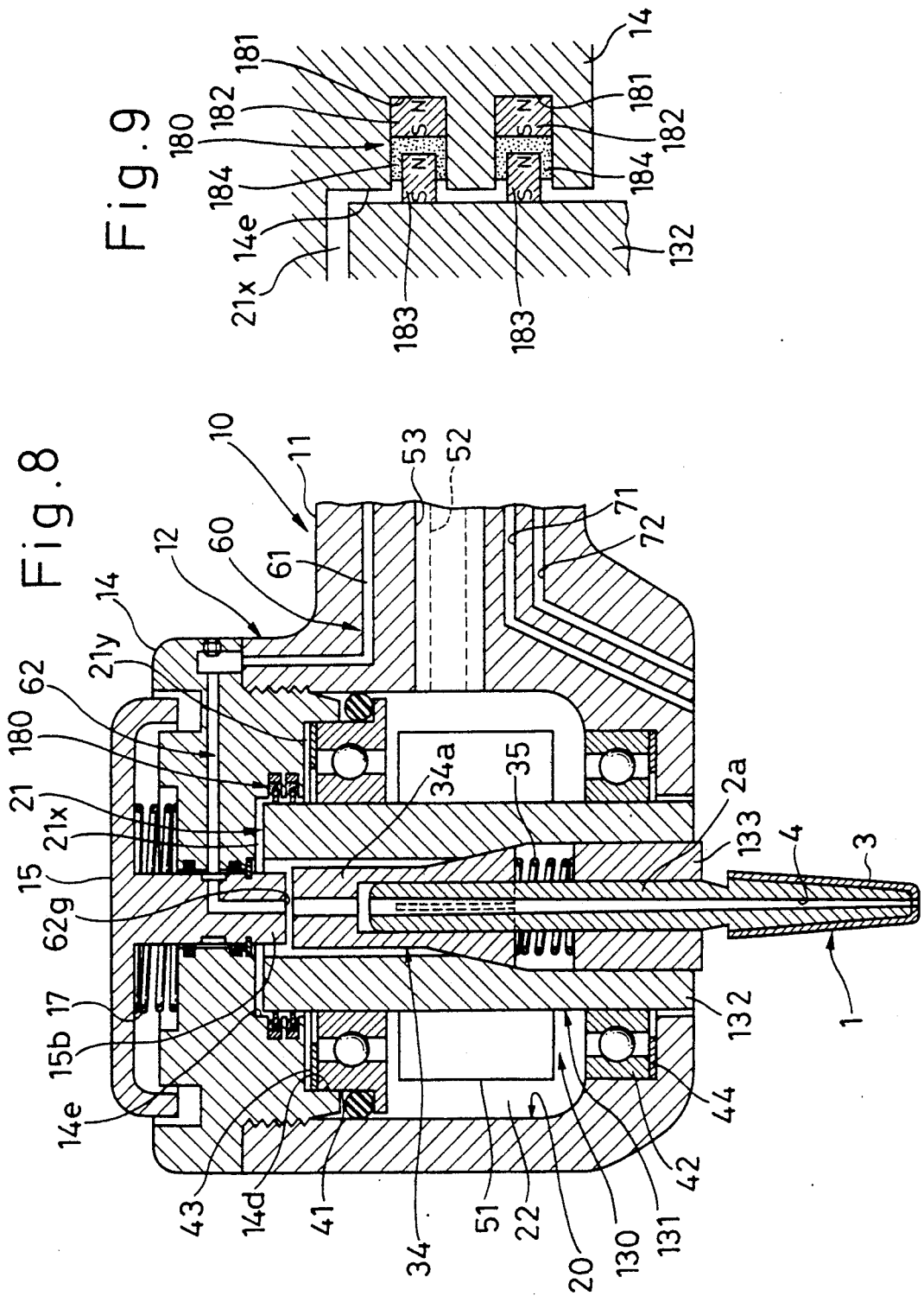

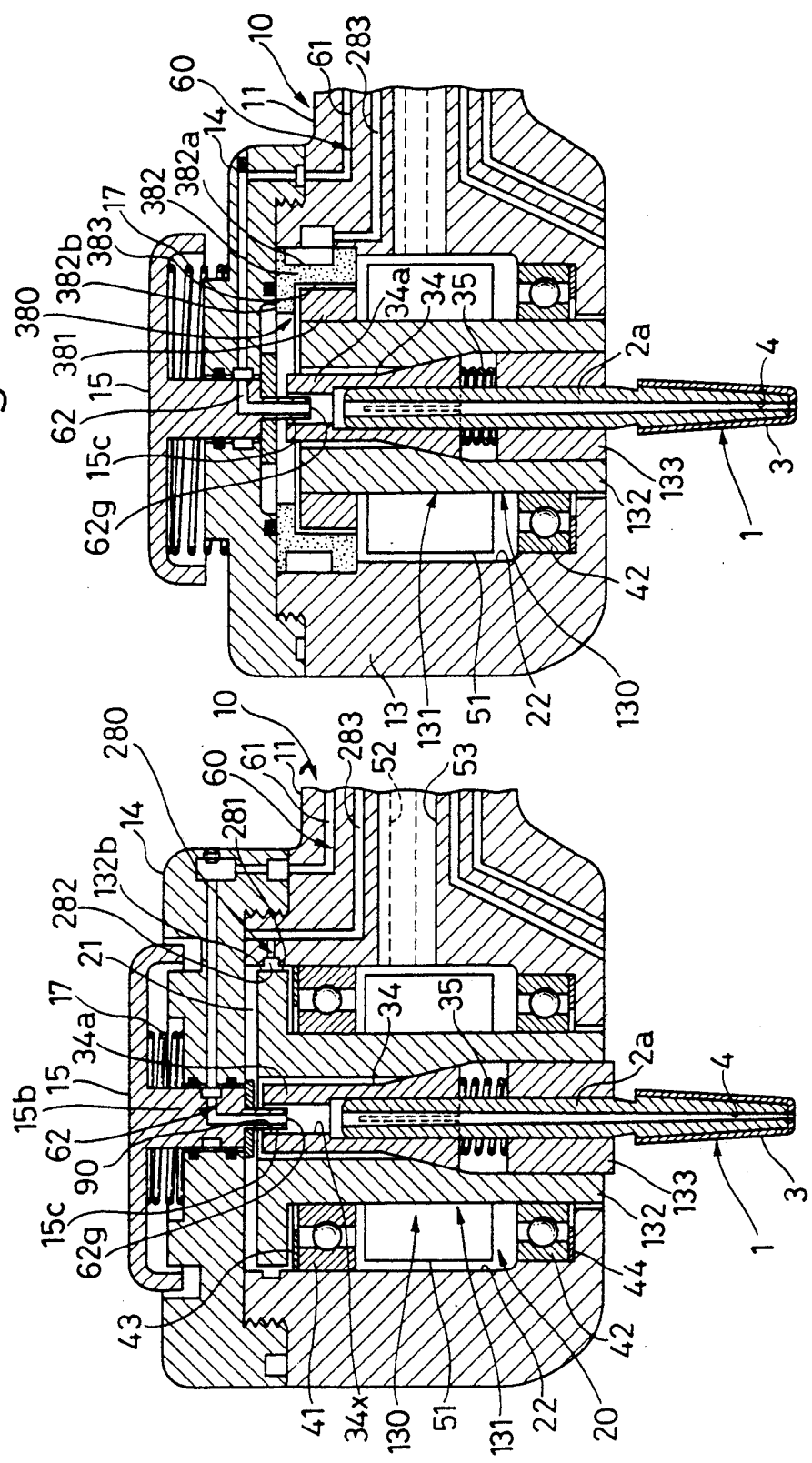

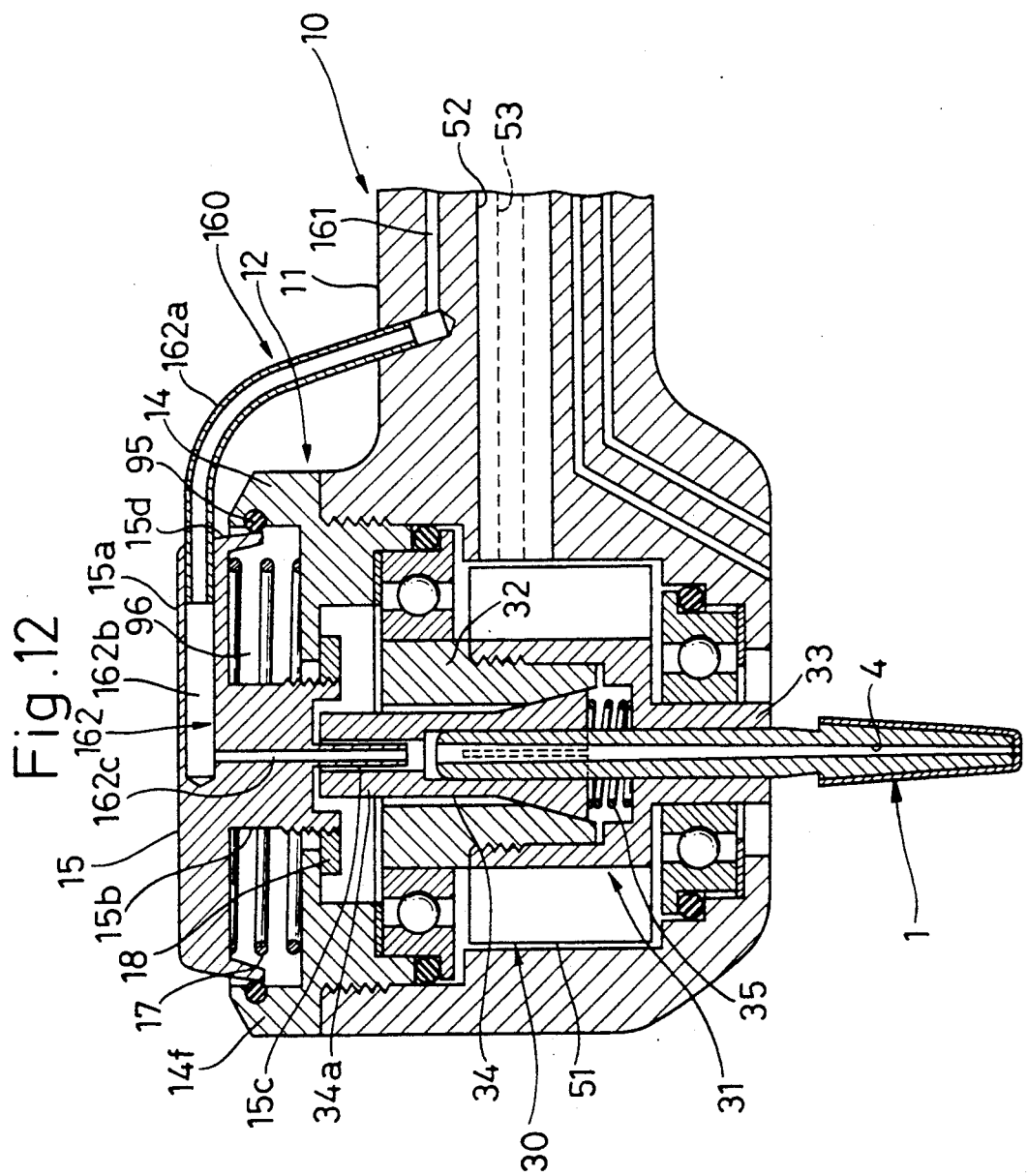

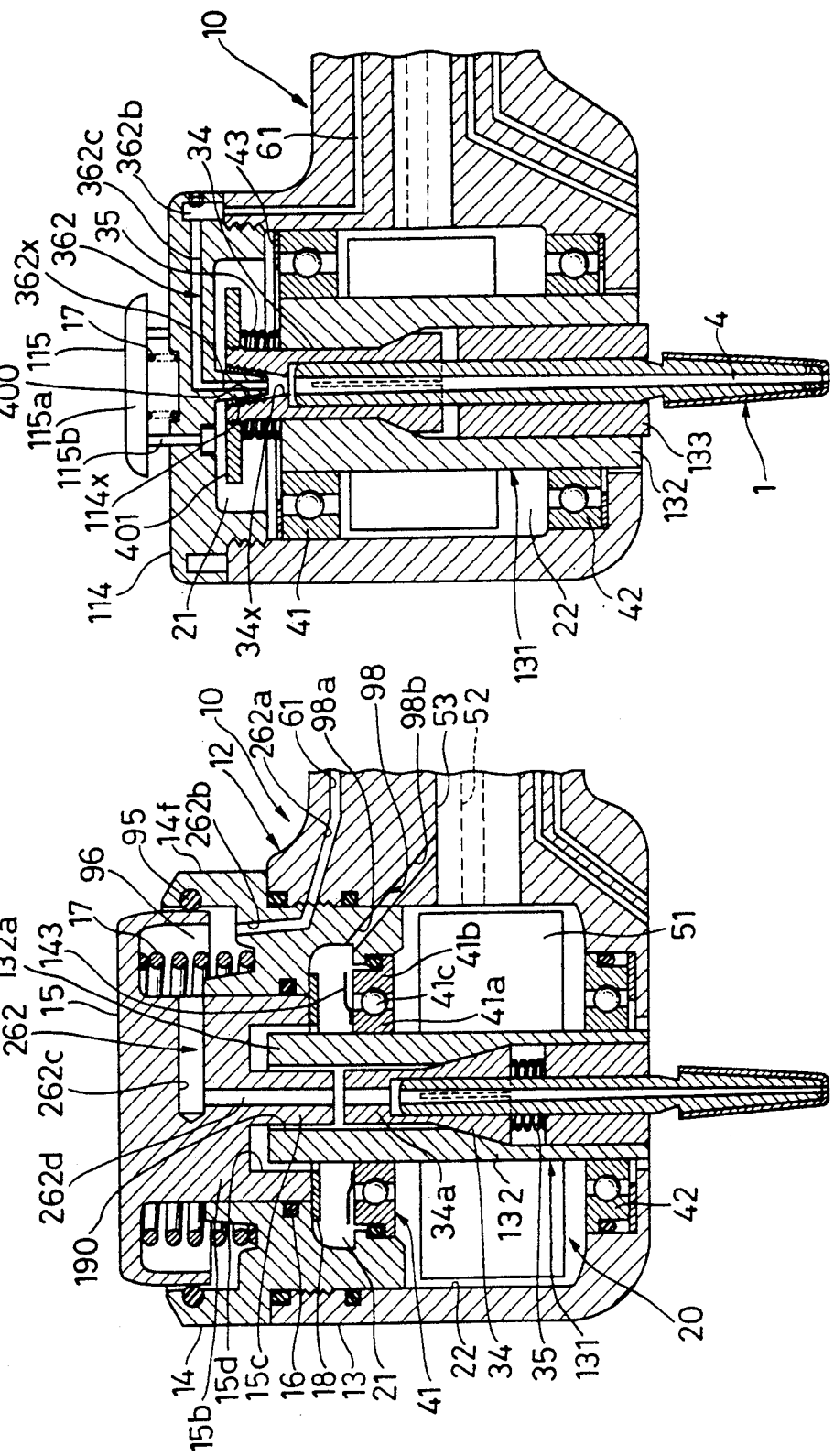

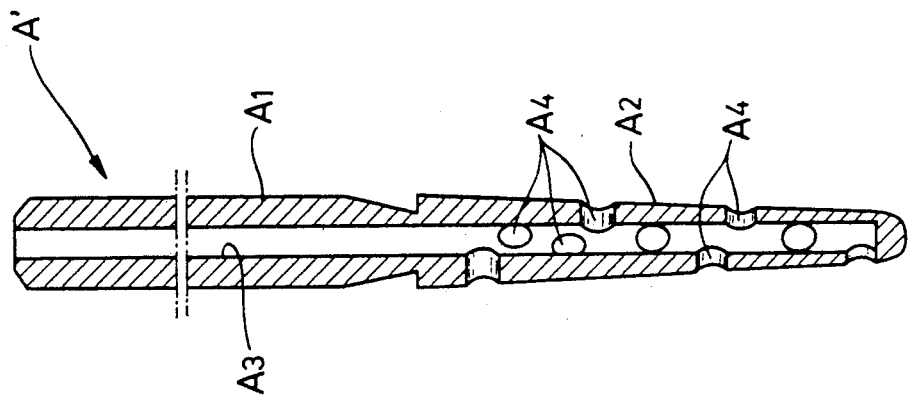
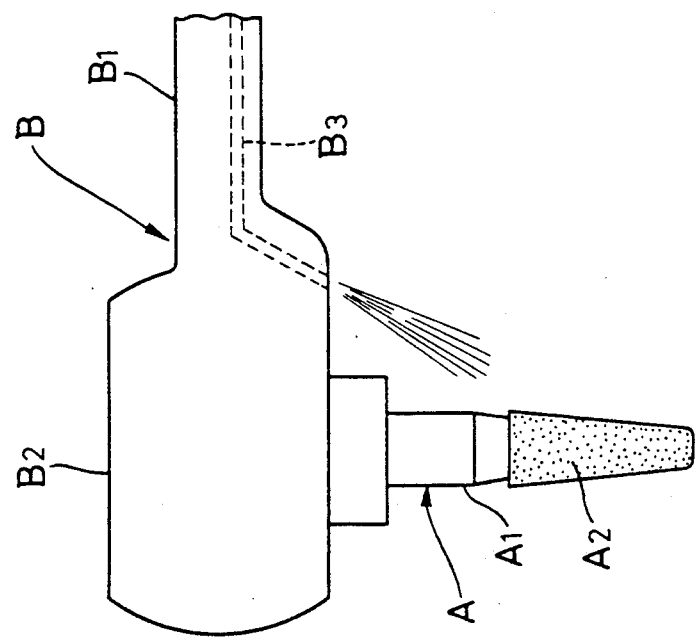

DENTAL BURR AND DENTAL HANDPIECE

BACKGROUND OF THE INVENTION

1. Field of the Invention

This invention relates to dental burrs and dental handpieces for rotatably holding such a dental burr.

2. Prior Art

FIG. 17 shows a conventional dental burr A and a conventional dental handpiece B both of which are of the general type, the dental handpiece being adapted to hold the dental burr A and drive the same for rotation about a longitudinal axis thereof to cut or bore the tooth of the patient.

The dental burr A comprises a shank portion $A_1$ at its rear portion and a cutting portion $A_2$ at its front portion, these two portions $A_1$ and $A_2$ having a common longitudinal axis or center line.

The handpiece B has a bar-like handgrip portion $B_1$ and a hollow head portion $B_2$ provided at a front end the handgrip portion $B_1$ The head portion $B_2$ contains therein a mechanism (not shown) for chucking the shank portion $A_1$ of the dental burr A and imparting a rotational movement thereto. The handpiece B also includes a cooling water passage $B_3$ which is formed in and extends along the handgrip portion $B_1$, the cooling water passage $B_3$ being connected at one end to a source of cooling water and opening at the other or distal end to a lower surface of the head portion $B_2$. This conventional handpiece B is disclosed in Japanese Laid-open (Kokai) Utility Model Application No. 56-51845.

When the dental burr A supported by the dental handpiece B is rotated at a high speed to cut the tooth of the patient, heat is generated at an area of contact between the cutting portion $A_2$ and the tooth. For this reason, during this cutting operation, the cooling water is injected toward the cutting portion $A_2$ of the dental burr A from either the distal end of the cooling water passage $B_3$ or a nozzle attached thereto to thereby cool the cutting portion $A_2$ and the tooth.

With the above dental burr A and handpiece B, however, an adequate cooling effect can not be achieved. The reason is that the cooling water is not sufficiently supplied to the area of contact between the cutting portion $A_2$ of the dental burr A and a surface defining a bore formed in the tooth by this cutting operation despite the fact that the heat is generated in this contact area.

The following disadvantages are caused by such insufficient cooling effect:

Firstly, the cutting portion $A_2$ of the dental burr A is subjected to high temperatures during the cutting operation and therefore undergoes a premature wear.

Secondly, the heat generated during the cutting operation stimulates the nerve of the tooth or the nerve of the gingiva or gum. As a result, the patient feels a pain. More specifically, for example, in the case of the treatment of a slightly-decayed tooth of which nerve has not yet been extracted, the heat thus generated is transmitted to the nerve of the tooth though the dental burr A is not in direct contact with this nerve. Also, in the case where the decayed portion of the tooth is bored by the dental burr in the vicinity of its root after extracting the tooth nerve, the heat is transmitted to the nerve of the gingiva. In these cases, anesthesia must be used to relieve the pain of the patient although the use of anesthesia is not desirable.

FIG. 18 shows a dental burr A' disclosed in U.S. Pat. No. 3,393,452. The dental burr A' has a cooling water passage $A_3$ formed therein and extending along its longitudinal axis. The cooling water passage $A_3$ opens at one end to a rear end face of a rear shank portion $A_1$ and terminates at the other end slightly short of a front end face of the cutting portion $A_2$. The dental burr A' also has a plurality of radially-extending ports $A_4$ formed through a peripheral wall of a front cutting portion $A_2$ of the dental burr A'. More specifically, each of the radial ports $A_4$ communicates at one end with the cooling water passage $A_3$ while the other end of the port $A_4$ opens to the outer peripheral surface of the cutting portion $A_2$.

In the dental burr A' of FIG. 18, the cooling water is supplied from the cooling water passage $A_3$ to the outer peripheral surface of the cutting portion $A_2$ through the radial ports $A_4$, and therefore the cooling water can be supplied to the area of contact between the outer peripheral surface of the cutting portion $A_2$ and the surface defining a bore formed in the tooth by the cutting portion $A_2$ to achieve an effective cooling operation.

However, the dental burr A' still has the following disadvantage:

When the dental burr A' is moved axially to deepen the bore being cut, the cooling water fails to be sufficiently supplied to the area of contact between the front end face of the cutting portion $A_4$ and the bottom face of the bore despite the fact that the heat is generated particularly at this contact area. As a result, such heat is not efficiently removed. Therefore, the stimulation of the tooth nerve or the gingiva nerve can not be restrained sufficiently. In addition, the wear of the front end face of the cutting portion $A_2$ can not duly be restrained.

Further, the above mentioned two dental burrs A and A' have a common drawback. More specifically, the speed of rotation of the front end face of the cutting portion $A_2$ is very low in the vicinity of the axis of rotation thereof, and therefore that portion of the front end face in the vicinity of the axis of rotation performs substantially no cutting function Therefore, when the dental burr A, A' is moved axially to deepen the bore being cut, said that portion of the front end face of the cutting portion $A_2$ is much resisted by the bottom face of the bore, so that a good cutting performance is not obtained.

As disclosed in Japanese Laid-Open (Kokai) Patent Application No. 58-65152, there is known prior to the present invention a handpiece which comprises a chuck mechanism for chucking a dental burr and a push button for releasing the chucking operation. As far as the inventor of the present invention knows, there is not known any handpiece of the type designed to supply the cooling water to such a dental burr provided with the cooling water passage as disclosed in the aforesaid U.S. Pat. No. 3,393,452.

SUMMARY OF THE INVENTION

It is therefore an object of this invention to provide a dental burr which achieves an excellent cooling effect and has good cutting performance.

Another object is to provide a dental handpiece of the type capable of supplying a cooling water to a dental burr provided with a cooling water passage.

A further object is to provide a dental handpiece having a sealing means for sealing against the cooling water.

According to one aspect of the present invention, there is provided a dental burr which comprises an elongated burr body having a front and a rear end and having an axis of rotation therethrough in a direction of the length thereof, the body having a shank portion defined by a rear end portion thereof and a cutting portion defined by a front end portion thereof, the body having a cooling water passage extending therethrough in coaxial relation to the body, the passage opening at one end to the rear end of the body and opening at the other end to the front end of the body, the opening of the passage in the front end of the body being disposed in an area including the axis of the body, and the one end of the passage being connectable to a source of cooling water.

According to another aspect of the invention, there is provided a dental handpiece for rotatably holding a dental burr, the dental burr including an elongated burr body having a front and a rear end and having an axis of rotation therethrough in a direction of the length thereof, the body having a shank portion defined by a rear end portion thereof and a cutting portion defined by a front end portion thereof, the body having a first cooling water passage extending along the axis of the body, the passage opening at one end to the rear end of the body and opening at the other end to an outer surface of the cutting portion of the body; the handpiece comprising:

(a) a handpiece body including a handgrip portion and a head portion provided at one end of the handgrip portion and having an internal space therein, the handpiece body having a second cooling water passage comprising a first sub-passage formed in the handgrip portion and a second sub-passage formed in the head portion, the first sub-passage being connectable to a source of cooling water, and the second sub-passage having a proximal end connected to the first sub-passage, the second sub-passage communicating at its distal end with the internal space of the head portion;

(b) support means mounted within the internal space of the head portion for supporting the shank portion of the dental burr in such a manner that the cutting portion of the dental burr extends outwardly from the head portion;

(c) bearing means for rotatably supporting the support means in such a manner that the burr body is rotatable about the axis of rotation thereof, the support means being disposed in spaced relation to an inner surface of the head portion defining the internal space;

(d) drive means for imparting a rotational movement to the support means; and (e) communicating passage means defined by part of the internal space of the head portion so as to communicate the distal end of the second sub-passage of the second cooling water passage with the one end of the first cooling water passage of the burr body.

BRIEF DESCRIPTION OF THE DRAWINGS

FIG. 1 is a longitudinal cross-sectional view of a dental burr provided in accordance with the present invention;

FIG. 2 is a view similar to FIG. 1 but showing a modified dental burr;

FIG. 3 is a front-elevational view of another modified dental burr;

FIG. 4 is a cross-sectional view taken along the line of IV—IV of FIG. 3;

FIG. 5 is a cross-sectional view of a dental handpiece provided in accordance with the present invention;

FIG. 6 is view similar to FIG. 5 but showing a modified handpiece;

FIG. 7 is an enlarged, cross-sectional view of a portion of the handpiece of FIG. 6, showing a seal means;

FIG. 8 is a view similar to FIG. 5 but showing another modified handpiece;

FIG. 9 is an enlarged, cross-sectional view of a portion of the handpiece of FIG. 8, showing a seal means;

FIGS. 10 to 15 are views similar to FIG. 5 but showing further modified handpieces, respectively;

FIG. 17 is a side-elevational view of a conventional dental handpiece using a conventional dental burr; and FIG. 18 is a longitudinal cross-sectional view of another conventional dental burr.

DESCRIPTION OF THE PREFERRED EMBODIMENTS OF THE INVENTION

Figure 16:
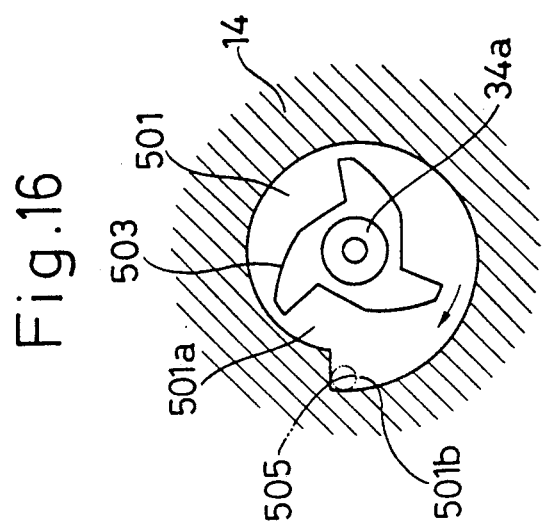
FIG. 16 is a cross-sectional view taken along the line XVI—XVI of FIG. 15.

The invention will now be described with reference to the drawings.

A dental burr 1 shown in FIG. 1 comprises an elongated body 2 made, for example, of stainless steel, the body 2 having a circular cross-section throughout the entire length thereof. The body 2 has a cylindrical shank portion 2a at its rear end portion, a tapered portion 2b at its front end portion which tapers toward its front end, and an intermediate tapered portion 2c interconnecting the shank portion 2a and the front tapered portion 2b and tapering toward the front end of the body 2. The outer peripheral surface of the front tapered portion 2b is relatively gently sloping while the outer peripheral surface of the intermediate tapered portion is relatively abruptly sloping. In other words, the cone angle of the intermediate tapered portion 2c is greater than that of the front tapered portion 2b. Diamond abrasive particles 3a are electrodeposited on the outer peripheral surface and front end face of the front tapered portion 2b to form a cutting portion 3. For example, the shank portion 2a has a diameter of 1.6 mm, and the front end of the cutting portion 3 has a diameter of about 0.8 mm.

The burr body 2 has a central cooling water passage or hole 4 formed therethrough and linearly extending along its longitudinal axis or center line. More specifically, the passage 4 extends coaxially with the burr body 2. The cooling water passage 4 opens at one end 4a to the rear end face of the shank portion 2a and opens at the other end 4b to the front end face of the cutting portion 3. The opening of the water cooling passage 4 formed in the other end 4b of the burr body 2 is disposed in an area including the axis of the burr body 2.

The cooling water passage 4 has a uniform-diameter portion 4c extending through the shank portion 2a and having a uniform diameter throughout the entire length of the shank portion 2a, and a tapered portion 4d extending through the cutting portion 3 and tapering toward the front end thereof.

Where the shank portion 2a has a diameter of 1.6 mm as described above, the uniform-diameter portion 4c has a diameter of 0.2 mm to 0.8 mm, and the opening 4b (i.e., the front end of the tapered portion 4d of the passage 4) has a diameter of 0.05 to 0.4 mm which is less than the diameter of the uniform diameter portion 4c.

The dental burr 1, attached to a handpiece later described, is designed to be rotated at a speed, for example, of 300,000 to 400,000 revolutions per minute. The rotating cutting portion 3 is brought into engagement with the tooth T, so that the diamond abrasive particles cut the tooth T to form a bore Ta therein. When the dental burr 1 is moved in a direction perpendicular to the axis of rotation thereof, a groove is formed in the tooth T.

During the cutting operation, the cooling water under pressure is introduced into the water cooling passage 4 from the opening 4a at the rear end face of the shank portion 2a, and is injected or discharged from the opening 4b at the front end face of the cutting portion 3, so that the dental burr 1 as well as the tooth T is cooled by the injected cooling water. More specifically, the cooling water injected from the front opening 4b removes the heat generated at an area of contact between the front end face of the cutting portion 3 and the bottom face of the bore Ta, and then is fed to an area of contact between the outer peripheral surface of the cutting portion 3 and the inner peripheral surface of the bore Ta to remove the heat generated at this contact area. Then, finally, the cooling water applied to the tooth T is discharged therefrom. Thus, the entire area of the tooth T from its bottom face to peripheral surface can be cooled, and the heat generated by the cutting operation is not transmitted to the nerve of the tooth or the nerve of the gingiva. Therefore, there is no need to apply anesthesia to the patient so long as the dental burr 1 is not brought into direct contact with these nerves.

In addition, since the front end face and outer peripheral surface of the cutting portion 3 disposed in cutting engagement with the tooth are positively cooled by the cooling water, these are not subjected to undue wear. Further, the cuttings cut from the tooth by the cutting portion 3 are removed by the cooling water, and therefore the cutting portion 3 is prevented from clogging, which keeps the heat generation to a low level.

The front opening 4b of the cooling water passage 4 is narrow, and therefore the cooling water can be discharged therefrom under a relatively high pressure and be positively applied between the bore Ta and the dental burr 1.

Further, the opening 4b is formed in the front end face of the dental burr body 2 and is disposed in the area including the axis of rotation of the burr body 2. Thus, the central portion of the front end face of the burr body 2 which is very low in rotational speed is removed. Therefore, even when the dental burr 1 is axially moved to deepen the bore Ta in the tooth T, the bottom face of the bore Ta offers a less resistance to the dental burr 1. Thus, the dental burr 1 has a good cutting performance.

A method of forming the dental burr 1 will now be described.

First, one end portion of a pipe is swaged into a tapered shape to provide the front tapered portion 2b of FIG. 1. At this time, the one or front end portion of the central bore of the pipe is tapered toward its front end, so that the central bore of the pipe constitutes the cooling water passage 4 of FIG. 1 having the tapered portion 4d. Then, the pipe is subjected to a cutting operation adjacent to the front tapered portion 2b to form the intermediate tapered portion 2c. The remainder, that is, the non-processed portion of the pipe serves as the shank portion 2a. Then, diamond abrasive particles are applied by electrodeposition to the entire outer surface of the front tapered portion 2b to form the cutting portion 3 of FIG. 1.

When the diamond abrasive particles are electrodeposited on the front tapered portion 2b, a layer of metal sometimes closes the small-diameter opening 4b of the cooling water passage 4. In such a case, a laser beam is applied to the center of the front end face of the cutting portion 3 to open the opening 4b thus closed by the metal layer.

A wire of an electrically non-conductive material may be inserted into the opening 4b when the above electrodeposition is carried out. In this case, the non-conductive wire suitably prevents the opening 4b from being closed by the metal layer.

Instead of the pipe, a cylindrical solid bar can be used as a stock, in which case a central bore is formed from a rear end face to front end face of the bar, for example, by an electrical discharge machining to provide the cooling water passage 4. An electrode used to create the central bore in the bar becomes worn as the electrical discharge machining proceeds, so that the resultant water cooling passage 4 is suitably tapered toward its front end, that is, the front opening 4b. After the formation of the water cooling passage 4 in the stock bar, the bar is processed or machined to obtain an outer configuration similar to that of the dental burr 1 of FIG. 1. The cooling water passage can be formed by drilling.

FIG. 2 shows a modified dental burr 1' which differs from the dental burr 1 of FIG. 1 only in that two auxiliary ports or passages 5 and 5 are formed through the peripheral wall of the cutting portion 3 adjacent to its front end and extend radially in diametrically opposite relation. Each of the two auxiliary ports 5 and 5 communicates at one end with the water cooling passage 4 while the other end opens to the outer peripheral surface of the cutting portion 3. With the dental burr 1', the cooling water is discharged from the front opening 4b of the cooling water passage 4 under a lower pressure as compared with the dental burr 1 of FIG. 1, but the auxiliary ports 5 and 5 can apply the cooling water to the outer peripheral surface of the cutting portion 3 more positively. Preferably, the diameter of each auxiliary port 5 should be substantially equal to or less than the diameter of the front opening 4b of the cooling water passage 4. The dental burr 1' of FIG. 2 can be formed by applying a laser beam to the front end portion of the cutting portion 3 of the dental burr 1 of FIG. 1 to provide the two auxiliary ports 5 and 5.

FIGS. 3 and 4 show another modified dental burr 1" which comprises an elongated body 6 of a circular cross-section made of cemented carbide. The body 6 has a shank portion 6a, a reduced diameter portion 6b and a tapered portion 6c interconnecting the shank portion 6a and the reduced diameter portion 6b. The outer surface of the front end portion of the body 6 (i.e., the front end portion of the reduced diameter portion 6b) is suitably processed or machined to provide a cutting portion 7. More specifically, a plurality of spiral grooves 7e are formed in the outer peripheral surface of the cutting portion 7, and a number of cutting sections 7a are provided along each spiral groove 7e in discrete manner. Each cutting section 7a has a cutting edge 7d defined by an intersection between a rake surface 7b and a relief surface 7c, the rake surface 7b and the relief surface 7c being constituted by a side wall of the groove 7e and the outer peripheral surface of the cutting portion 7, respectively. A cooling water passage 8 extends through the body 6 from the rear end face of the shank portion 6a to the front end face of the cutting portion 7 in coaxial relation to the body 6, the cooling water passage 8 being of a uniform cross-section throughout its entire length. A pair of diametrically-opposite auxiliary ports 9 and 9 are formed through the peripheral wall of the front end portion of the cutting portion 7, each auxiliary port 9 communicating at one end with the cooling water passage 8 and opening at the other end to the relief surface 7c.

Dental handpieces for use with the above-mentioned dental burrs 1, 1' and 1" will now be described.

FIG. 5 shows a dental handpiece according to a first embodiment of the present invention. This dental handpiece comprises a body 10 which includes a bar-like handgrip portion 11 and a hollow head portion provided at a front end of the handgrip portion 11. Although not shown in the drawings, the handgrip portion 11 is bent at a predetermined angle intermediate opposite ends thereof, and the rear portion thereof remote from the head portion 12 is adapted to be gripped by the operator.

The head portion 12 comprises a tubular portion 13 formed integrally with the handgrip portion 11 and having open upper and lower ends, a cap 14 threaded into the upper open end of the tubular portion 13, and a push button 15 attached to the cap 14 for purposes later described. The cap 14 and the push button 15 cooperate with each other to provided a closure means 19 for closing the open upper end of the tubular portion 13. The head portion 12 has an internal space 20 defined by the inner peripheral surface of the tubular portion 13, a bottom surface of the cap 14 and a bottom surface of the push button 15.

The tubular portion 13 has an axis disposed vertically and extending perpendicular to the longitudinal axis of the front end portion of the handgrip portion 1. An externally-threaded portion 14a formed on the outer peripheral surface of the cap 14 are threaded into an internally-threaded portion 13a formed on the upper peripheral surface of the tubular portion 13 at its upper end portion. The outer peripheral surface of the cap 14 is stepped adjacent to the upper end of the threaded portion 14a to provide a should 14b, and the upper end surface 13b of the tubular portion 13 is held in firm contact with the shoulder 14b. The cap 14 has a central hole 14c formed therethrough and has a recess 14d formed in the bottom face thereof.

The push bottom 15 comprises a disc-shaped pressure-receiving portion 15a and a stem portion 15b formed on a central portion of the receiving portion 15a and extending downwardly therefrom, the pressure-receiving portion 15a being adapted to be pressed by the finger. The stem portion 15b is received in the central hole 14c of the cap 14 for movement therealong. An O-ring 16 is interposed between the outer peripheral surface of the stem portion 15b and the inner peripheral surface of the central hole 14c to provide a seal therebetween.

A compression coil spring 17 is wound around the stem portion 15b and acts between the lower surface of the receiving portion 15a of the push button 15 and the upper surface of the cap 14 to normally urge the push button 15 upwardly. A retainer 18 in the form of an annular plate is fixedly secured to the lower end of the stem portion 15b of the push button 15 and held against the lower surface of the cap 14 (the upper surface of the recess 14d) so as to limit the upward movement of the push button 15 and to prevent the push button 15 from becoming disengaged from the cap 14.

A support means 30 for supporting the dental burr is mounted within the internal space 20 and is rotatably supported by a pair of upper and lower bearings 41 and 42.

The support means 30 comprises a rotatable body 31 of a tubular shape disposed in coaxial relation to the tubular portion 13 of the head portion 12. The rotatable body 31 comprises an upper tubular member 32 and a lower tubular member 33 threadedly connected to the upper tubular member 32. The lower tubular member 33 has an upper greater-diameter portion 33a, lower reduced-diameter portion 33b, and a radial wall portion 33c interconnecting the upper and lower portions 33a and 33b.

The support means 30 further comprises a chuck member 34 received in the upper tubular member 32 of rotatable body 31. The chuck member 34 has an upper tubular portion 34a and a lower tubular portion 34b extending downwardly from the upper portion 34a. A plurality of slits 34c are formed through the lower tubular portion 34b and extend throughout substantially the entire length thereof, so that the lower tubular portion 34b has a plurality of longitudinal fins 34d. The lower section 34e of the lower tubular portion 34b is tapering from its lower end and is radially contractible by virtue of the provision of the slits 34c. A lower inner peripheral surface 32a of the upper tubular member 32 of the rotatable body 31 is correspondingly tapered from its lower end so that the tapered lower section 34e can be snugly fitted in its radially contracted condition in the tapered surface 32a.

A compression coil spring 35 is received in the upper portion 33a of the lower tubular member 33 of the rotatable member 31 and acts between the lower end face of the chuck member 34 and the radial wall portion 33c of the lower tubular member 33 to normally urge the chuck member 34 upwardly.

The upper bearing 41 comprises an inner ring 41a fixedly mounted around the outer peripheral surface of the upper tubular member 32 of the rotatable body 31 adjacent to the upper end thereof, an outer ring 41b fixedly mounted on the inner peripheral surface of the recess 14d of the cap 14, and a number of balls 41c interposed between the coaxially-disposed inner and outer rings 41a and 41b. The lower bearing 42 comprises an inner ring 42a fixedly mounted around the outer peripheral surface of the reduced-diameter portion 33b of the lower tubular member 33 of the rotatable member 31, an outer ring 42b fixedly mounted on the inner peripheral surface of the lower open end of the tubular portion 13 of the handpiece body 10, and a number of balls 42c interposed between the coaxially-disposed inner and outer rings 42a and 42b.

An annular seal plate 43 is fixedly secured to the upper end of the outer ring 41b of the upper bearing 41 in coaxial relation thereto. The seal plate 43 almost closes the space or gap between the inner and outer rings 41a and 41b from above, and the inner peripheral edge of the seal plate 43 is slightly spaced radially outwardly form the upper end of the inner ring 41b.

Another annular seal plate 44 is interposed between the lower end of the outer ring 42b of the lower bearing 42 and an upper surface of a peripheral flange 13c radially inwardly extending from the lower open end of the tubular portion 13, and is disposed coaxially therewith. The seal plate 43 almost closes the space between the inner and outer rings 42a and 42b from below, and the inner peripheral edge of the seal plate 44 is slightly spaced radially outwardly form the lower end of the inner ring 42a.

A pair of O-rings 45 and 45 are interposed between the upper bearing 41 and the inner peripheral surface of the tubular portion 13 and between the lower bearing 42 and the inner peripheral surface of the tubular portion 13, respectively.

The upper bearing 41 cooperates with the rotatable body 31 to divide the internal space 20 of the head portion 12 into an upper chamber 21 and a lower chamber 22.

The support means 30 is rotated by a drive means 50 which comprises blades 51 mounted on the outer periphery of the lower tubular member 33 of the rotatable member 31 and disposed within the lower chamber 22, an air supply passage 52 formed in the handgrip portion 11. Each of the air supply and discharge passages 52 and 53 extends in the direction of the length of the handgrip portion 11, and opens at one end to the rear end of the handgrip portion 11, and opens at the other end to the inner peripheral surface of the lower chamber 22 of the head portion 12. The one end of the air supply passage 52 is connected to a source 55 of compressed air in the form of an air compressor via a fitting (not shown), a flexible tube (not shown) and a valve 54. The one end of the air discharge passage 53 opens to the atmosphere or is connected to a discharge device via a flexible tube.

The handpiece body 10 has a cooling water passage 60 which comprises a first cooling water passage 61 formed in the handgrip portion 11 and a second cooling water passage 62 formed in the head portion 12. The first water cooling passage 61 opens at one end to the rear end of the handgrip portion 11 and is connected to a source 64 of the cooling water, such as a faucet (tap) of the city water or a pump, via a fitting (now shown), a flexible tube (not shown) and a valve 63.

The second cooling water passage 62 has a first portion 62a formed in the upper portion of the peripheral wall of the tubular portion 13 and extending parallel to the axis of the tubular portion 13. One end of the first portion 62a is connected to the other end of the first cooling water passage 61 while the other of the first portion 62a opens to the upper end surface 13b of the tubular portion 13.

The second cooling water passage 62 also has a second portion 62b and a third portion 62c both of which are formed in the cap 14. The second portion 62b is in the form of an annular groove formed in the shoulder 14b of the cap 14 and is connected to the first portion 62a. The third portion 62c extends radially of the cap 14 and is connected at one end to the second portion 62b while the other end opens to the inner peripheral surface of the central hole 14c of the cap 14.

The second cooling water passage 62 further has a fourth portion 62d, a fifth portion 62e and a sixth portion 62f all of which are formed in the stem portion 15b of the push button 15. The fourth portion 62d is in the form of an annular groove formed in the peripheral surface of the stem portion 15b and is connected to the other end of the third portion 62c. The fifth portion 62e extends radially of the stem portion 15b and is connected at one end to the fourth portion 62d, the other end of the fifth portion 62e lying one the axis or center lien of the stem portion 15b. The sixth portion 62f extends coaxially with the stem portion 15b and is connected at one end to the fifth portion 62e, the sixth portion 62f opening at the other end 62g to the lower end face of the stem portion 15b. The opening 62g lies on the axis or center line of the chuck member 34.

Additionally, another cooling water passage 71 and another compressed air supply passage 72 are formed in the handpiece body 10 so that conventional burrs can be used with this dental handpiece. Each of these passages 71 and 72 extends longitudinally of the handgrip portion 11 and opens at one end to the rear end of the handgrip portion 11 while the other end opens to the lower surface of the head portion 12 and is directed toward the axis of the tubular portion 13. The one end of the cooling water passage 71 is connected to the cooling water source 64 via a valve 73, and the one end of the compressed air supply passage 72 is connected to the compressed air source 55 via a valve 74.

In operation, when the push button 15 is depressed against the vias of the compression spring 17, the stem portion 15b is brought into engagement with the upper end of the chuck member 34 to move the same downwardly against the bias of the compression spring 35. As a result, the tapered lower section 34e of the chuck member 34 having the plurality of fins 34d is disengaged from the tapered surface 32a of the rotatable body 31 to be radially expanded. In this condition, for example, the shank portion 2a of the dental burr 1 of FIG. 1 is inserted into the tapered lower section 34e through the reduced-diameter portion 33b of the lower tubular member 33 of the rotatable body 31. Then, the depression of the push button 15 is released to return it upwardly to its initial position under the influence of the compression spring 17. At the same time, the chuck member 34 is urged upwardly by the compression spring 35, so that the tapered section 34e of the chuck member 34 is snugly fitted in the tapered surface 32a of the rotatable body 31 and contracted radially. As a result, the shank portion 2a of the dental burr 1 is chucked or clamped by the thus contracted tapered section 34e. In this condition, the dental burr 1 is disposed in coaxial relation to the chuck member 34, the rotatable body 31 and the tubular portion 13 of the head portion 12, and the cutting portion 3 of the dental burr 1 is projected downwardly from the lower surface of the head portion 12.

Then, when the valve is opened, the compressed air is supplied from the compressed air source 55 to the lower chamber 22 of the internal space 20 via the air supply passage 52 and impinges on the blades 5 of the rotatable body 31, so that the support means 30 supporting the dental burr 1 is rotated at high speed together therewith. Then, when the valve 63 is opened, the cooling water is supplied from the cooling water source 64 via the cooling water passage 60 and is introduced into the upper chamber 21 through the front or distal end opening 62g of the passage 60 to fill the upper chamber 21. The cooling water thus filled in the upper chamber 21 flows into the water cooling passage 4 of the dental burr 1 through a communicating passage 34x of the upper tubular portion 34a of the chuck member 34 and the rear opening 4a of the passage 4, and is discharged therefrom through its front opening 4b.

In this manner, the dental burr 1 is rotated, with the cooling water injected from the front opening 4b of the cooling water passage 4, to carry out a dental treatment.

Because the support means 30 and the dental burr 1 are rotated at high speed, it is not possible to hold them in sliding contact with the surface defining the internal space 20. Therefore, the cooling water passage 60 of the handpiece cannot be connected directly to the cooling water passage 4 of the dental burr 1. For this reason, in this embodiment, the upper chamber 21 serves as a passage means for communicating the cooling water passage 60 with the cooling water passage 4.

The cooling water filled in the upper chamber 21 is j prevented by the seal plate 43 from intruding into the upper bearing 41, and therefore this cooing water will not be evaporated by the frictional heat developing between the balls 41c of the upper bearing 41 and each of the associated rings 41a and 41b. This prevents the upper bearing 41 from rust due to steam which would otherwise develop by contact of the cooling water with the bearing 41. Since the cooling water does not pass through the upper bearing 41, the lower bearing 42 is also free from rust. This ensures a high speed rotational movement of the support means 30 for a prolonged period of time. In addition, since the cooling water will not intrude into the lower chamber 22, the rotation of the blades 51 are not affected at all.

The seal plate 43 is slightly spaced from the inner ring 41a of the upper bearing 41 to avoid frictional heat which would generated if they were in contact with each other. It is preferred that the pressure of the compressed air within the lower chamber 22 should be slightly higher than the pressure of the cooling water within the upper chamber 21 to positively prevent the cooling water from passing through this small space or gap between the seal plate 43 and the inner ring 41a. For the same reason, preferably, the supply of the compressed air should precede the supply of the cooling water, and the supply of the compressed air should be ceased after the supply of the cooling water is stopped.

The cooling water discharged from the dental burr 1 may be splashed over the head portion 12 of the handpiece during the cutting operation by the rotating dental burr 1. In this case, the splash of the cooling water is prevented from intruding into the lower bearing 42 by the seal plate 44 attached thereto.

After the dental treatment, the supply of the cooling water is stopped, and then the supply of the compressed air is ceased. Then, the push button 15 is depressed to radially expand the tapered section 34e of the chuck member 34 having the fins 34d, and in this condition, the dental burr 1 is removed from the handpiece. After the removal of the dental burr 1, the depression of the push button 15 is released to bring the handpiece in its initial condition.

Several modified handpieces according to the present invention will now be described. Those parts of these embodiments which are identical to or correspond to the parts in their preceding embodiments will be denoted by the respective same reference numerals, and detailed explanation thereof will be omitted.

FIGS. 6 and 7 show a handpiece according to a second embodiment of the invention. The second embodiment differs from the first embodiment of FIG. 5 in that a seal means 80 is provided and in that a support means 130 replaces the support means 30.

The support means 130 comprises a rotatable body 131 which includes a longer tubular member 132 and a shorter tubular member 133 fitted in a lower end portion of the longer tubular member 132 and fixed thereto. The longer tubular member 132 has at a central portion a tapered inner peripheral surface 132a which is normally fitted on the tapered section 34e of the chuck member 34. The compression coil spring 35 for urging the chuck member 34 upwardly acts between the lower end of the chuck member 34 and the upper end of the shorter tubular member 133. p The annular seal means 80 provides a seal between the upper end face of the longer tubular member 132 and the lower surface of the cap 14. The seal means 80 will now be described in further detail. The upper end face of the longer tubular member 132 is spaced from the lower surface of the cap 14 to form a small space or gap 85 therebetween. An annular groove 81 is formed in the upper end face of the longer tubular member 132, and a first permanent magnet 82 of a ring-shape is fixedly mounted in the lower portion of the groove 81, the magnet 82 being equal in width to the groove 81. A second permanent magnet 83 of a ring-shape is fixedly secured to the lower surface of the cap 14 in slightly spaced, registered relation to the first permanent magnet 82. The second permanent magnet 83 is smaller in width than the groove 81 and is received at its lower end portion in the groove 81. Each of the first and second magnets 82 and 83 is magnetized in the direction of the axis thereof, and these two magnets 82 and 83 are so arranged that the opposed surfaces of the magnets 82 and 83 have the opposite magnetic poles, respectively. A magnetic fluid 84 is filled in the groove 81, and therefore the magnetic fluid is filled in the space between the first and second magnets 82 and 83.

The upper chamber 21 is divided by the seal means 80 into a first sub-chamber 21x disposed inside the seal means 80 into a second sub-chamber 21y disposed outside of the seal means 80. The cooling water discharged from the distal end 62g of the cooling water passage 60 fills the first sub-chamber 21x and is further fed to the cooling water passage 4 of the dental burr 1 through the communicating passage 34x of the upper tubular portion 34a of the chuck member 34. Thus, the first sub-chamber 21x serves as a passage means for communicating the cooling water passage 60 with the cooling water passage 4.

The cooling water within the first sub-chamber 21x is positively prevented by the seal means 80 from entering the second sub-chamber 21y and therefore is prevented from reaching the upper and lower bearings 41 and 42.

In the seal means 80, the magnetic fluid 84 performs a sealing function, and the first and second permanent magnets 82 and 83 spaced from each other retain or hold the magnetic fluid 84. Thus, the seal means 80 provides no rigid part-to-rigid part contact, and therefore the support means 130 can be rotated very smoothly.

One of the first and second permanent magnets 82 and 83 can be replaced by a ring made of a magnetic material.

FIGS. 8 and 9 show a handpiece according to a third embodiment of the invention.

The third embodiment differs from the second embodiment of FIGS. 6 and 7 in that a seal means 180 replaces the seal means 80. In this embodiment, a recess 14e of a smaller diameter is formed in the upper surface of a recess 14d of a cap 14 in coaxial relation thereto, and an upper end portion of a longer tubular member 132 is received in the recess 14e, the outer peripheral surface of the longer tubular member 132 being slightly spaced from the inner peripheral surface of the recess 14e to form a narrow annular space therebetween. A stem portion 15 of a push button 15 extends into the upper end portion of the longer tubular member 132.

The seal means 180 will now be described in further detail. A pair of upper and lower annular grooves 181 and 181 are formed in the inner peripheral surface of the recess 14e in slightly spaced relation to each other, and a ring-shaped permanent magnet 182 is fixedly mounted in the bottom of each groove 181, the magnet 182 being substantially equal in width to the groove 181. Another pair of upper and lower permanent magnets 183 and 183 of a ring-shape are fixedly mounted on the outer peripheral surface of the upper end portion of the longer tubular member 132 in slightly spaced, registered relation to the upper and lower permanent magnets 182 and 182, respectively. Each permanent magnet 183 is smaller in width than the groove 181 and is received at the outer peripheral portion thereof in the groove 181. Each permanent magnet 182 as well as each permanent magnet 183 is magnetized in the radial direction, and each pair of registered magnets 182 and 183 are so arranged that the opposed surfaces of the magnets 182 and 183 have the opposite magnetic poles, respectively. A magnetic fluid 184 is filled in each groove 81, and therefore the magnetic fluid is filled in the space between each pair of registered magnets 182 and 183.

FIG. 10 shows a handpiece according to a fourth embodiment of the invention. The fourth embodiment differs from the second embodiment of FIG. 6 in two points. Referring to the first difference, a hollow cylindrical projection 15c projects downwardly from the lower end of a stem portion 15b of a push button 15 in coaxial relation thereto and extends into the upper tubular portion 34a of the chuck member 34. The projection 15c is not in contact with the upper tubular portion 34a. More specifically, the outer peripheral surface of the projection 15c is spaced from the inner peripheral surface of the upper tubular portion 34a to form an annular space 90 therebetween. The lower open end of the internal bore of the projection 15c serves as a distal end 62g of the second cooling water passage 62 in the head portion 12.

The second difference is that there is provided a seal means 280 utilizing compressed air. More specifically, a longer tubular member 132 of a rotatable member 131 has an outwardly-directed peripheral flange 132b formed at its upper end. The outer peripheral surface of the flange 132b is slightly spaced from the inner peripheral surface of the tubular portion 13 of the handpiece body 10 to form a narrow annular space 281 therebetween. An annular groove 282 is formed in the inner peripheral surface of the tubular portion 13 adjacent to its upper end and is disposed in opposed relation to the outer peripheral surface of the flange 132b. A compressed air passage 283 is connected at one end to the annular groove 282. The compressed air passage 283 extends through the handgrip portion 11 of the handpiece body 10 along the length thereof and opens at the other end to the rear end of the handgrip portion 11, the other end being connected to the compressed air source 55 (FIG. 5).

In the fourth embodiment, the cooling water, discharged from the distal end 62g of the second cooling water passage provided at the lower end of the projection 15c, passes through the communicating passage 34x of the upper tubular portion 34a of the chuck member 34 into the cooling water passage 4 of the dental burr 1. Thus, the communicating passage 34x serves as a passage means for communicating the water cooling passage 60 with the water cooling passage 4.

Part of the cooling water discharged from the distal end 62g of the second cooling water passage 62 leaks through the annular space 90 into an upper chamber 21 to fill it.

The compressed air is supplied to the annular groove 282 from the compressed air passage 282, and is further injected to the upper chamber 21 through the narrow space 281 formed between the outer peripheral surface of the flange 132b and the inner peripheral surface of the tubular portion 13. The compressed air injected to the upper chamber 21 suitably prevents the cooling water from intruding into the upper bearing 41 and the lower chamber 22 (and hence the lower bearing 42). It is preferred that the space 281 should be as narrow as possible to block the passage of the cooling water so long as the flange 132b is kept out of contact with the tubular portion 13. For example, the space 281 is 0.01 to 0.05 mm.

The compressed air supplied to the space 281 has a pressure higher than the pressure of the cooling water supplied to the upper chamber 21 to thereby seal the space 281 positively.

It is also preferred that the space 90 between the projection 15c of the push button 15 and the upper tubular portion 34a of the chuck member 34 should be as narrow as possible so long as they are kept out of contact with each other. By doing so, a pressure drop at the space 90 prevents the pressure of the compressed air from being applied to the cooling water within the upper tubular portion 34a through the upper chamber 21, thereby ensuring that the supply of the cooling water will not be affected.

FIG. 11 shows a handpiece according to a fifth embodiment of the invention which is similar to the fourth embodiment of FIG. 10 but is provided with a different type of seal means 380 utilizing the compressed air. The seal means 380 also serves as an upper bearing.

More specifically, an inner ring 381 is fixedly mounted on an outer peripheral surface of a longer tubular member 132 of a rotatable body 131 at an upper end thereof. An outer ring 382 is fixedly mounted on the inner peripheral surface of the tubular portion 13 adjacent to the upper end thereof and disposed around the inner ring 381. The outer ring 382 is porous and is made, for example, of porous sintered metal or ceramics, the outer ring 382 having an annular groove 382a formed in the outer peripheral surface thereof and connected to a compressed air passage 283. The outer ring 382 has an inwardly-directed peripheral flange 382b formed at the upper end thereof and overlying the inner ring 381. The outer peripheral surface of the inner ring 381 is closely spaced from the inner peripheral surface of the outer ring 382, and the upper surface of the inner ring 381 is slightly spaced from the lower surface of the flange 382b. Therefore, a very narrow annular space 383 is formed between the inner and outer rings 381 and 382. A coating for blocking the passage of the compressed air is applied to all the surfaces of the outer ring 382 except for those surfaces that define the annular groove 382a and for those surfaces that cooperate with the inner ring 381 to define the space 383.

In the fifth embodiment, the compressed air is supplied from the compressed air passage 283 to the annular groove 382a of the outer ring 382 and is further fed to the annular space 383 through a large number of pores in the body of the outer ring 382. The thus fed compressed air seals the annular space 383 to prevent the cooling water from intruding into the lower chamber 22 and hence the lower bearing 42. Also, this compressed air supports or bears the inner ring 381 in a manner to permit its rotation relative to the outer ring 382 in a non-contact fashion. Thus, the compressed air in the annular space 383 functions as a bearing.

FIG. 12 shows a handpiece according to a sixth embodiment of the invention which is provided with a cooling water passage 160 replaces the cooling water passage 60 in the preceding embodiments. More specifically, one end of a flexible tube 162a is fixedly fitted in a hole formed in the front end portion of the handgrip 11 so as to communicate with a first cooling water passage 161 formed in a handgrip portion 11. The other end of the flexible tube 162a is fixedly fitted in a hole or passage 162b formed in a pressure-receiving portion 15a of a push button 15, the hole 162b extending radially or the pressure receiving portion 15a and opening at one end to the side or peripheral surface thereof. A second cooling water passage 162 formed in a head portion 12 has the hole 162b in the pressure receiving portion 15a, and a passage 162c connected to the hole 162b and formed in and extending axially of the push button 15. The axial passage 162c extends through a cylindrical projection 15c projecting axially downwardly from a lower surface of a stem portion 15b and opens at its lower end to the lower end of the projection 15c. Thus, the first and second cooling water passages 161 and 162 are interconnected by the flexible tube 162a.

In the sixth embodiment, a downwardly-directed peripheral flange or wall 15d is formed on the lower peripheral edge of the pressure receiving portion 15a of the push button 15. The flange 15d is received in an upper peripheral wall 14f of a cap 14 in closely spaced relation thereto, and an O-ring 95 is mounted on the inner peripheral surface of the upper peripheral wall 14f to provide a seal between the flange 15d and the peripheral wall 14f, so that there is provided a closed spring-receiving chamber 96 in which a compression coil spring 17 is accommodated.

FIG. 13 shows a handpiece according to a seventh embodiment of the invention in which a second cooling water passage 262 formed in a head portion 12 has a first portion 262a formed in a tubular portion 13 and opening to the inner peripheral surface of the tubular portion 13, a second portion 262b formed in a cap 14 and communicating the first portion 262a with a spring-receiving chamber 96, a third portion 262c formed in a stem portion 15b of a push button 15 and extending radially thereof, and a fourth portion 262d extending from the third portion 262c axially of the push button 15.

In the seventh embodiment, the push button 15 has a downwardly-opening recess 15d formed in the lower end face thereof, and a hollow cylindrical projection 15c extending downwardly from the upper surface of the recess 15d at its center. An upper end portion 132a of a longer tubular member 132 of a rotatable member 131 is received in the recess 15d of the push button 15. The projection 15c is received in the upper end portion 132a of the longer tubular member 132 in closely spaced relation thereto so that a very narrow annular space 190 is formed therebetween.

An annular seal plate 143 is fixedly secured at its inner peripheral portion to an upper surface of an inner ring 41a of an upper bearing 41. The seal plate 143 is stepped intermediate the inner and outer peripheries thereof, and its outer peripheral portion covers or overlies an outer ring 41b of the upper bearing 41 in closely spaced relation thereto.

An upper chamber 21 of the internal space 20 communicates with the air discharge passage 53 via a communication passage 98 which has a first portion 98a formed in a cap 14 and a second portion 98b formed in a tubular portion 13.

In the seventh embodiment, when part of the cooling water leaks through the annular space 190 formed between the projection 15c of the push button 15 and the longer tubular member 132 of the rotatable member 131, such leaking cooling water is atomized by the rotational force of the longer tubular member 132 to be dissipated toward the upper chamber 21. On the other hand, the compressed air is supplied to the upper chamber 21 from a lower chamber 22 through the upper bearing 41 and the space between the seal plate 143 and the outer ring 41b. Therefore, the cooling water is prevented from intruding into the upper bearing 41 and the lower chamber 22 (and hence the lower bearing 42). In addition, since the seal plate 143 is fixedly mounted on the inner ring 41a for rotation therewith, the cooling water applied onto the rotating seal plate 143 is dissipated under the centrifugal force exerted thereon. This further ensures a positive sealing effect. The atomized cooling water is fed to the air discharge passage 53 via the communication passage 98 and is discharged exteriorly of the handpiece.

FIG. 14 shows a handpiece according to an eighth embodiment of the invention in which a hollow tapered projection 114x extending downwardly from a lower surface of a cap 114 at its center. A second cooling water passage 362 provided in the head portion 12 is formed in the cap 114. The second cooling water passage 362 has an annular first portion 362b, a second portion 362c extending radially of the cap 114, and a third portion 362x extending axially of the cap 114. The central bore of the hollow tapered projection 114x constitutes part of the third portion 362x. A push button 115 includes a pressure-receiving portion 115a, and a plurality of stem portions 115b extending downwardly from the lower surface of the receiving portion 115a in radially spaced relation to the center of the cap 114.

An inner peripheral surface of an upper tubular portion 34a of a chuck member 34 is tapered downwardly at its upper end portion, and the downwardly-tapered projection 114x of the cap 114 is received in the tapered upper portion of the inner peripheral surface of the upper tubular portion 34a in closely spaced relation thereto. A spiral projection or ridge 400 is formed on the tapered upper portion of the inner peripheral surface of the upper tubular portion 34a.

An annular receiving plate 401 is fixedly mounted on the outer peripheral surface of the upper tubular portion 34a adjacent to the upper end thereof through a threaded connection. A compression coil spring 35 is wound around the upper tubular portion 34a and acts between the lower surface of the receiving plate 401 and an upper end of a longer tubular member 132 of a rotatable member 131 to urge the chuck member 34 upwardly.

In the eighth embodiment, the cooling water injected from the lower end of the taper projection 114x is fed to the cooling water passage 4 of the dental burr 1 through the communicating passage 34x of the upper tubular portion 34a. At this time, part of the cooling water tends to leak exteriorly of the chuck member 34 through the space between the upper tubular portion 34a and the tapered projection 114x. However, the chuck member 34 is rotated, so that the spiral projection 400 serves as a pump to downwardly draw the cooling water present in the space between the upper tubular portion 34a and the tapered projection 114x. As a result, the cooling water will not leak into the upper chamber 21 and therefore will not intrude into the upper bearing 41 and the lower chamber 22 (and hence the lower bearing 42).

In the eighth embodiment, when the push button 115 is depressed, the lower ends of the stem portions 115 are brought into engagement with the receiving plate 401 to urge the chuck member 34 downwardly, so that the chucking of the dental burr 1 by the chuck member 34 is released.

The upper portion of the inner peripheral surface of the upper tubular portion 34a may not be tapered and may instead be of a uniform cross-section along its length, in which case the tapered projection 114c is also replaced by a cylindrical projection having a uniform outer diameter throughout its entire length.

Figure 15:
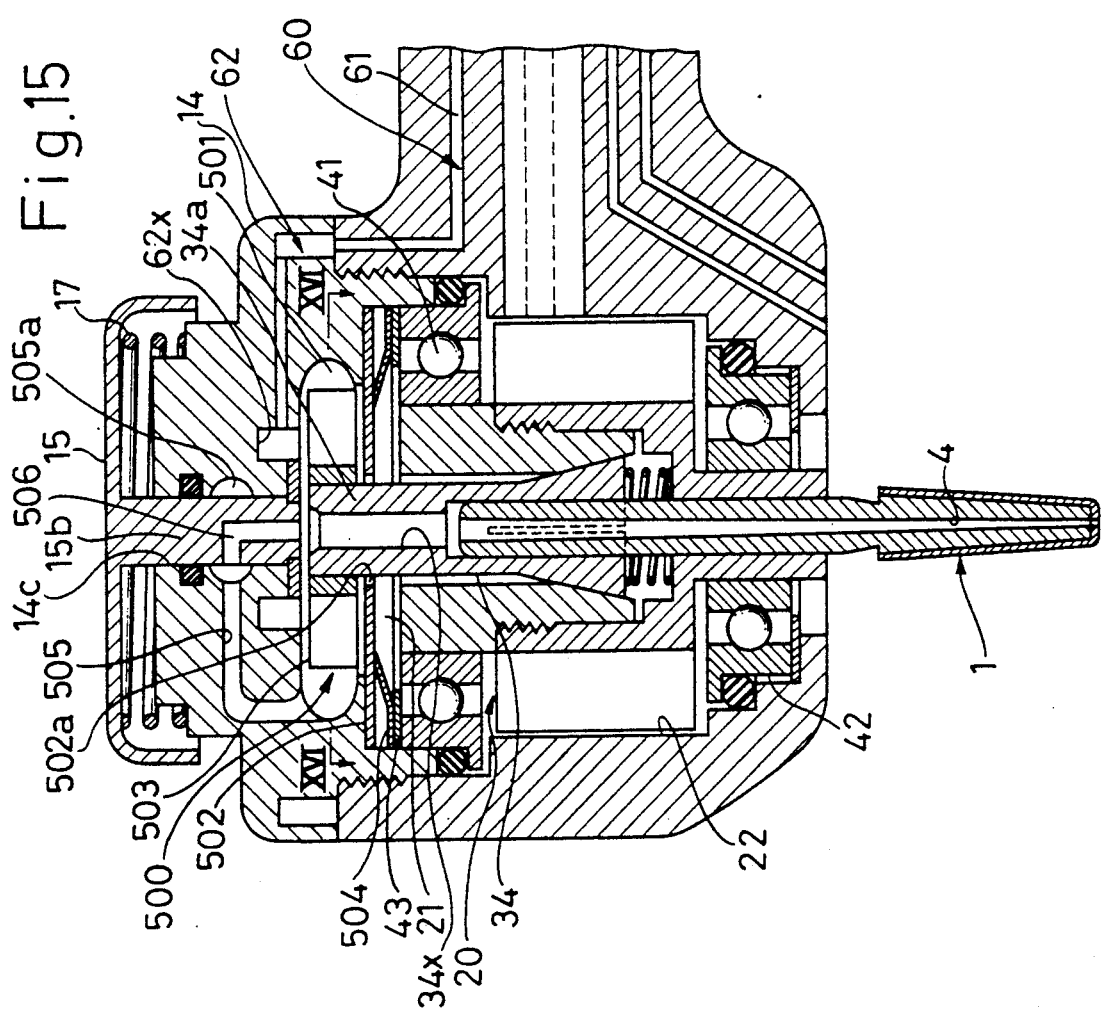

FIGS. 15 and 16 show a handpiece according to a ninth embodiment of the invention which is provided with a different type of pump means 500. More specifically, a pump chamber 501 is formed in a lower surface of a cap 14, the pump chamber 501 constituting part of the internal space 20. As shown in FIG. 16, the peripheral surface of the pump chamber 501 is curved about the axis of rotation of a chuck member 34, and the curvature of this curved peripheral surface (i.e., its radius with respect to the axis of rotation of the chuck member 34) is increasing gradually in a clockwise direction. With this arrangement, the pump chamber 501 has a minimum-radius portion 501a and a maximum-radius portion 501b, and the inner peripheral surface of the pump chamber 501 is stepped at the boundary between the minimum-radius portion 501a and the maximum-radius portion 501b. The pump chamber 501 is isolated from an upper chamber 21 by a partition plate 502. The partition plate 502 has a central aperture 502a through which an upper end portion of an upper tubular portion 34a of the chuck member 34 extends into the pump chamber 501 in closely spaced relation to the peripheral edge defining the aperture 502a. A plurality of blades 503 are fixedly mounted around the upper end portion of the upper tubular portion 34a disposed within the pump chamber 501. Preferably, a space between the partition plate 502 and the blades 503 should be as narrow as possible. The partition plate 502 is supported by a belleville spring 504 acting between the partition plate 502 and the seal plate 43 so that the partition plate 502 is vertically movable.

A second water cooling passage 62 of a cooling water passage 60 formed in a head portion 12 terminates in an annular groove 62x formed in the cap 14, the annular groove 62x being disposed immediately above the pump chamber 501 and opening thereto adjacent to the upper tubular portion 34a.

Communication passages 505 and 506 are formed in the cap 14 and a push button 15, respectively. The communication passage 505 in the cap 14 opens at one end to the upper wall of the maximum-radius portion 501a of the pump chamber 501, and terminates at the other end in an annular groove 505a opening to a central hole 14c of the cap 14. The communication passage 506 in a stem portion 15b of the push button 15 communicates at one end with the communicating passage 505 and opens at the other end to the lower end of the stem portion 15b, the lower end of the stem portion 15b being disposed in facing relation to the upper tubular portion 34a of the chuck member 34.

In the ninth embodiment, the cooling water, injected into the pump chamber 501 from the annular groove 62x of the cooling water passage 60, is directed toward the inner peripheral surface of the pump chamber 501 by the rotating blades 503 which is rotatable in a clockwise direction (FIG. 16). The cooling water thus deflected is fed from the maximum-radius portion 501b of the pump chamber 501 to the cooling water chamber 4 of the dental burr 1 via the communicating passages 505 and 506 and the communicating passage 34x of the upper tubular portion 34a of the chuck member 34.

In the ninth embodiment, the pump chamber 501 and the communicating passages 505 and 506 jointly constitute a passage means for communicating the cooling water passage 60 with the cooling water passage 4.

As mentioned above, the narrow annular space is formed between the outer periphery of the upper tubular portion 34a of the chuck member 34 and the peripheral edge of the central aperture 502a of the partition plate 502. During the operation, a negative pressure is created in this annular space because of the rotational movement of the blades 503. Therefore, the cooling water will not leak into the upper chamber 21 through this annular space. In addition, the actuation of the pump means 500 supplies the cooling water to the cooling water passage 4 of the dental burr 1 under an increased pressure.

When the push button 15 is depressed, the stem portion 15b is brought into engagement with the upper end of the chuck member 34. A further depression of the push button 15 causes the chuck member 34 to move downwardly, thereby releasing the chucking of the dental burr 1 by the chuck member 34. At this time, the blades 503 fixedly mounted on the chuck member 34 urges the partition plate 502 downwardly against the bias of the belleville spring 504. Thus, since the partition plate 502 is movable in the direction of movement of the chuck member 34, the chuck member 34 has a sufficient stroke of movement for releasing its chucking operation.

In addition to the dental burr 1 of FIG. 1, the dental burrs of FIGS. 2 and 3 as well as the dental burr of the above-mentioned U.S. patent can be used with any of the above-described handpieces according to the invention.

What is claimed is:

1. A dental handpiece for rotatably holding a dental burr, said dental burr including an elongated burr body having a front and a rear end and having an axis of rotation therethrough in a direction of a length thereof, said body having a shank portion defined by a rear end portion thereof and a cutting portion defined by a front end portion thereof, said body having a first cooling water passage extending along the axis of said body, said passage opening at one end to the rear end of said body and opening at the other end to an outer surface of said cutting portion of said body; said handpiece comprising:

(a) a handpiece body including a handgrip portion and a head portion provided at one end of said handgrip portion and having an internal space therein, said head portion comprising a tubular portion formed at the one end of said handgrip portion and having opposite open ends through one of which said cutting portion of said dental burr is adapted to extend outwardly of said handpiece body, said head portion also comprising a cap for closing the other open end of said tubular portion and a push button mounted on said cap for movement relative to said cap, said push button having a stem portion slidably extending along an axis of said tubular portion through said cap into said internal space, said handpiece body having a second cooling water passage comprising a first sub-passage and a second sub-passage, said first sub-passage being formed in said handgrip portion and connectable to a source of cooling water, said second sub-passage having a proximal end connected to said first sub-passage, said second sub-passage being formed in said tubular portion of said head portion, said cap and said push button, said second sub-passage having a distal portion which is formed in said stem portion and extends along a longitudinal axis of said stem portion, said second sub-passage opening at its distal end to an end face of said stem portion of said push button;

(b) support means mounted within said internal space of said head portion for supporting said shank portion of said dental burr in such a manner that said cutting portion of said dental burr extends outwardly from said head portion, said support means comprising a tubular rotatable body extending along the axis of said tubular portion, said support means also comprising chuck means received in said rotatable body so as to releasably chuck said shank portion of said dental burr, said stem portion of said push button being operatively engageable with said chuck means so as to release the chucking of said shank portion by said chuck means when said push button is depressed, said distal portion of said second sub-passage of said second cooling water passage being on the axis of said first cooling water passage of said dental burr when said dental burr is supported by said support means, the distal end of said second sub-passage being communicated with said first cooling water passage;

(c) bearing means for rotatably supporting said tubular rotatable body of said support means in such a manner that said burr body is rotatable about the axis of rotation thereof, said support means being disposed in spaced relation to an inner surface of said head portion defining said internal space; and (d) drive means for imparting a rotational movement to said support means.

2. A dental handpiece according to claim 1, in which said support means includes a tubular rotatable portion disposed in facing relation to said inner surface of said stem portion of said push button, said stem portion having a projection extending therefrom into said tubular rotatable portion, said projection being disposed in coaxial relation to said first cooling water passage of said dental burr when said dental burr is supported by said support means, and said distal portion of said second sub-passage of said second cooling water passage extending through said projection along the axis of said projection.

3. A dental handpiece according to claim 2, in which said tubular rotatable portion is formed in said chuck means of said support means.

4. A dental handpiece according to claim 2, in which said tubular rotatable portion constitutes part of said rotatable body of said support means, said projection of said stem portion of said push button being operatively engageable with said chuck means so as to release the checking of said shank portion by said chuck means when said push button is depressed.

5. A dental handpiece for rotatably holding a dental burr, said dental burr including an elongated burr body having a front and a rear end and having an axis of rotation therethrough in a direction of a length thereof, said body having a shank portion defined by a rear end portion thereof and a cutting portion defined by a front end portion thereof, said body having a first cooling water passage extending along the axis of said body, and said passage opening at one end to the rear end of said body and opening at the other end of an outer surface of said cutting portion of said body; said handpiece comprising:

(a) a handpiece body including a handgrip portion and a head portion provided at one end of said handgrip portion and having an internal space therein, said head portion comprising a tubular portion formed at the one end of said handgrip portion and having opposite open ends through one of which said cutting portion of said dental burr is adapted to extend outwardly of said handpiece body, said head portion also comprising closure means for closing the other open end of said tubular portion, said handpiece body having a second cooing water passage comprising a first sub-passage and a second sub-passage, said first sub-passage being formed in said handgrip portion and connectable to a source of cooling water, said second sub-passage being formed in said tubular portion and closure means of said head portion, said second sub-passage having a proximal end connected to said first sub-passage and a distal end opening to an inner face of said closure means;

(b) support means mounted within said internal space of said head portion for supporting said shank portion of said dental burr in such a manner that said cutting portion of said dental burr extends outwardly from said head portion, the distal end of said second sub-passage being communicated with said first cooling water passage when said dental burr is supported by said support means;

(c) bearing means for rotatably supporting said support means in such a manner that said burr body is rotatable about the axis of rotation thereof, said support means being disposed in spaced relation to an inner surface of said head portion defining said internal space; and (d) drive means for imparting a rotational movement to said support means;

wherein said support means includes a tubular rotatable portion disposed in facing relation to said inner surface of said closure means, said closure means having a projection formed an said inner surface thereof and extending therefrom into said tubular rotatable portion, said projection being disposed in coaxial relation to said first cooling water passage of said dental burr when said dental burr is supported by said support means, and said second sub-passage of said second cooling water passage having a distal portion extending through said projection along the axis of said projection; and wherein pump means is provided between an inner peripheral surface of said tubular rotatable portion of said support means and an outer peripheral surface of said projection of said closure means, said pump means achieving its pumping action by rotation of said tubular rotatable portion relative to said projection so that the cooling water disposed between the inner peripheral surface of said tubular rotatable portion and the outer peripheral surface of said projection is drawn by positive pressure toward said first cooling water passage of said cental burr.

6. A dental handpiece according to claim 5, in which said pump means comprises a spiral groove formed in the inner peripheral surface of said tubular rotatable portion of said support means.

7. A dental handpiece for rotatably holding a dental burr, said dental burr including an elongated burr body having a front and a rear end and having an axis of rotation therethrough in a direction of a length thereof, said body having a shank portion defined by a rear end portion thereof and a cutting portion defined by a front end portion thereof, said body having a first cooling water passage extending along the axis of said body, and said passage opening at one end to the rear end of said body and opening at the other end of an outer surface of said cutting portion of said body; said handpiece comprising:

(a) a handpiece body including a handgrip portion and a head portion provided at one end of said handgrip portion and having an internal space therein, said head portion comprising a tubular portion formed at the one end of said handgrip portion and having opposite open ends through one of which said cutting portion of said dental burr is adapted to extend outwardly of said handpiece body, said head portion also comprising closure means for closing the other open end of said tubular portion, said handpiece body having a second cooling water passage comprising a first sub-passage and a second sub-passage, said first sub-passage being formed in said handgrip portion and connectable to a source of cooling water, said second sub-passage being formed in said tubular portion and closure means of said head portion, said second sub-passage having a proximal end connected to said first sub-passage and a distal end opening to an inner face of said closure means.

(b) support means mounted within said internal space of said head portion for supporting said shank portion of said dental burr in such a manner that said cutting portion of said dental burr extends outwardly from said head portion, the distal end of said second sub-passage being communicated with said first cooling water passage when said dental burr is supported by said support means;

(c) bearing means for rotatably supporting said support means in such a manner that said burr body is rotatable about the axis of rotation thereof, said support means being disposed in spaced relation to an inner surface of said head portion defining said internal space; and (d) drive means for imparting a rotational movement to said support means;

wherein said support means includes a tubular rotatable portion disposed in facing relation to said inner surface of said closure means, said closure means having a projection formed an said inner surface thereof and extending therefrom into said tubular rotatable portion, said projection being disposed in coaxial relation to said first cooling water passage of said dental burr when said dental burr is supported by said support means, and said second sub-passage of said second cooling water passage having a distal portion extending through said projection along the axis of said projection;

wherein said pump means is provided between an inner peripheral surface of said tubular rotatable portion of said support means and an outer peripheral surface of said projection of said closure means so that the cooling water disposed between the inner peripheral surface of said tubular rotatable portion and the outer peripheral surface of said projection is drawn by positive pressure toward said first cooling water passage of said cental burr by said pump means when said tubular rotatable portion is rotated; and wherein said closure means comprises a cap attached to the other open end of said tubular portion of said head portion and a push button mounted on said cap for movement relative said cap, said push button having a stem means slidably extending through said cap into said internal space and disposed in radially spaced relation to said projection; said support means comprising a tubular rotatable body supported by said bearing means so as to be rotatable about a longitudinal axis thereof extending along the axis of said tubular portion of said head portion, said support means also comprising chuck means received in said rotatable body so as to releasably chuck said shank portion of said dental burr; and said stem of said push button being operatively engageable with said chuck means so as to release the chucking of said shank portion by said chuck means when said push button is depressed.

8. A dental hand piece according to claim 7, in which said stem means of said push button comprise a plurality of stem portions.

9. A dental handpiece according to claim 8, in which said tubular rotatable portion is formed in said chuck means, said tubular rotatable portion being provided with a flange on an outer periphery thereon, said stem portions of said push button being operatively engageable with said flange so as to release the checking of said shank portion by said chuck means when said push button is depressed.

10. A dental handpiece for rotatably holding a dental burr, said dental burr including an elongated burr body having a front and a rear end and having an axis of rotation therethrough in a direction of a length thereof, said body having a shank portion defined by a rear end portion thereof and a cutting portion defined by a front end portion thereof, said body having a first cooling water passage extending along the axis of said body, said passage opening at one end to the rear end of said body and opening at the other end to an outer surface of said cutting portion of said body; said handpiece comprising:

(a) a handpiece body including a handgrip portion and a head portion provided at one end of said handgrip portion and having an internal space therein, said head portion comprising a tubular portion formed at the one end of said handgrip portion and having opposite open ends through one of which said cutting portion of said dental burr is adapted to extend outwardly of said handpiece body, said head portion also comprising closure means for closing the other open end of said tubular portion, said handpiece body having a second cooling water passage comprising a first sub-passage and a second sub-passage, said first sub-passage being formed in said handgrip portion and connectable to a source of cooling water, said second sub-passage being formed in said tubular portion and closure means of said head portion, said second sub-passage having a proximal end connected to said first sub-passage and a distal end opening to an inner face of said closure means;
(b) support means mounted within said internal space of said head portion for supporting said shank portion of said dental burr in such a manner that said cutting portion of said dental burr extends outwardly from said head portion, the distal end of said second sub-passage being communicated with said first cooling water passage when said dental burr is supported by said support means;
(c) bearing means for rotatably supporting said support means in such a manner that said burr body is rotatable about the axis of rotation thereof, said support means being disposed in spaced relation to an inner surface of said head portion defining said internal space; and
(d) drive means for imparting a rotational movement to said support means;
in which said bearing means comprises a pair of first and second bearing members spaced from each other along the axis of said tubular portion and disposed coaxially with said tubular portion said second bearing member being disposed at said one end of said tubular portion, said first bearing member being disposed between said closure means and said one end of said tubular portion so that said first bearing member cooperates with said support means to divide said internal space along the axis of said tubular portion into a first chamber closure to said closure means and a second chamber remote from said closure means, there being provided a plurality of blades fixedly mounted around said support means and disposed within said second chamber, said handpiece body having an air supply passage for supplying compressed air to said second chamber so that the compressed air acts on said blades to rotate said support means, said handpiece body also having an air discharge passage for discharging the compressed air from said second chamber, and said drive means comprising said blades and said air supply and discharge passages; and
in which said air supply passage and said air discharge passage extend in a longitudinal direction of said handgrip portion toward a proximal end of said handgrip portion, said handpiece body having a communicating passage formed therein and communicating said first chamber of said internal space with said air discharge passage, said projection of said closure means being received in said tubular rotatable portion in closely spaced relation thereto, whereby the cooling water, leaking from said tubular rotatable portion into said first chamber through a space between said tubular rotatable portion and said projection, flows into said air discharge passage through said communicating passage to be discharged exteriorly of said handpiece body.

* * * * *